United States Patent [19]

Zoueki

[11] Patent Number: 4,693,573
[45] Date of Patent: Sep. 15, 1987

[54] UNIVERSAL FRAME CENTERING, HOLDING AND MEASURING DEVICE

[76] Inventor: Georges Zoueki, 4812 Verdun, Verdun, Quebec, Canada, H4G 1N1

[21] Appl. No.: 838,111

[22] Filed: Mar. 10, 1986

[51] Int. Cl.$^4$ ............................................. A61B 3/10
[52] U.S. Cl. ....................................... 351/204; 33/200
[58] Field of Search ....................... 351/204, 227, 231; 33/200

[56] References Cited

U.S. PATENT DOCUMENTS 2,491,312 12/1949 Henry et al. ........................ 351/204
4,252,419 2/1981 Padula, II et al. .................. 351/204

Primary Examiner—Rodney B. Bovernick
Assistant Examiner—P. M. Dzierzynski
Attorney, Agent, or Firm—Robic, Robic & Associates

[57] ABSTRACT

An universal frame centering, holding and measuring device for use by an optician to transcribe and check a distance interpupillary distance a reading interpupillary distance, a segment height measured onto a customer, directly and precisely on a set of lenses mounted on a frame. The device comprises a base having a longitudinal axis, on which the frame may be positioned in flat position. A central pin supporting a vertical cylinder having such diameter as to fit within the bridge of the frame, projects from the base. A frame holder is slidably mounted onto the base. The frame holder is movable along the longitudinal axis of the base and comprises a vertical front wall extending perpendicularly to the longitudinal axis of the base. The frame holder is pressed toward the central pin in such a manner as to hold the frame in substantially rigid position between the vertical front wall of the frame holder and the vertical cylinder mounted onto the central pin, with this vertical cylinder inserted into the bridge portion of the frame. A pair of rulers are slidably mounted on the base, parallel to its longitudinal axis in such a manner as to extend under the two lenses mounted on the frame respectively. A set of vertical graduation is provided on each ruler, each vertical graduation indicating the distance separating it from the central pin and being useful for transcribing onto the lenses and checking the distance P.D. or reading P.D. of the customer. A set of horizontal graduations is also provided on each ruler, these horizontal graduations being useful for transcribing on the lenses the segments heights or progressive horizontal cross line of the customer.

14 Claims, 3 Drawing Figures

UNIVERSAL FRAME CENTERING, HOLDING AND MEASURING DEVICE

BACKGROUND OF THE INVENTION (a) Field of the Invention

The present invention relates to an universal frame centering, holding and measuring device for use by an optician to transcribe measurements taken onto a customer, such as a distance interpupillary distance (distance P.D.), a reading interpupillary distance (reading P.D.), a segment height, directly, symmetrically and precisely on a set of lenses mounted on a frame, such as, for example, on the demonstration lenses that are generally provided with a new frame, or on the customer lenses of his or her own frame.

The invention also relates to a universal frame centering, holding and measuring device that can also be used to read and check a monocular interpupillary distance or a non-symmetrical interpupillary distance, in order to verify a completed job.

(b) Brief Description of the Related Art and Objects of the Invention

It is of common practice for opticians, once their customers have selected the frame in which they want their prescription lenses to be fitted, to measure the distance between the two pupils of the customer while the same is looking at distance (distance P.D.) in order to make the optical centers of the lenses correspond with the customer's pupils and thus avoid a non-desired prismatic effect.

A problem with such a measurement is that an important number of persons have a non-symmetrical interpupillary distance, the distance between the right eye center and the nose center of these persons being indeed different from the distance between the left eye center and the nose center.

A first object of the present invention is to provide a device for use in transcribing with a fine permanent ink felt pen, the P.D. measurements made on a customer symmetrically and precisely onto the demonstration lenses contained in a new frame, or on any other lenses, such a transcription allowing the optician, once the frame is re-installed on the customer's face, to notice a nonsymmetrical or any P.D. measuring mistakes, and then to correct them in such a way that the final result is a set of vertical lines made on the lenses and crossing each pupil, each line corresponding to the normal position of each eye with respect to the frame when the customer is looking away at distance (distance vertical P.D. line).

It is also well known that the value of the close or reading interpupillary distance (reading P.D.) that is the value of the distance between the eye centers when reading, is always shorter by about 2 to 4 mm, than the dist. P.D. Therefore, for bifocals wearers, in addition to fitting the distance optical centers on the distance vertical P.D. lines of their customer's eyes in order to avoid a non-desired prismatic effect, the opticians must also fit the lateral bifocal segment center onto the reading vertical P.D. line of each eye in order to provide the customer with a maximum field of vision for reading.

In addition to measuring the interpupillary distance whenever a bifocal is prescribed, it is also of common practice for opticians to measure the desired bifocal top level whose "ideal" height is below the lower lid top. This ideal height which is called "segment height", has to be measured on the reading vertical P.D. line from the lower lid level down to the bottom of the frame inside the ring. However, occupation or habits of the customers may require modifications of these standards. Indeed, this measurement is very critical and the customer's head position as well as the position of the looked point may substantially affect the results. Therefore, it is usually recommended in practise to compare the customer segment heights to which he is used, with the measurements just taken by the optician.

Another object of the present invention is to provide a device for use in transcribing the above mentioned segment height measurements on the demonstration lenses with the help of a fine permanent ink felt pen, in order to allow the optician to compare these measurements. After such a transcription, re-installation of the frame with the marked lenses on the customer's face will allow the optician to notice and quantitatively evaluate the amount of difference between the old and new glasses by mere alternance on the customer's face of these old and new frames, thereby making it possible to correct or adjust the measurments on the new glasses, if necessary.

It is also known that in all bifocals types, the bifocal segment height must be measured on the reading vertical P.D. line. In most of what is called "progressive lenses", the fitting "cross" or center must however be measured on the distance vertical P.D. line.

A further object of the present invention is to provide a device which is sufficiently universal to provide easy transcription on demonstration lenses of bifocal segment heights and heights of the fitting crosses in the case of progressive lenses, depending on the customer's requirements and need.

It is also of common practice that, once a frame is selected and the distance and reading P.D., the height of segments for bifocals or the height of the fitting crosses for progressive lenses have been established, the optician has to determine with precision the smallest size of uncut lenses that are required to realize the mounting. The main objects of this particular operation are as follows:

1. to reduce the cost price, a lens of smaller diameter being always less expensive;
2. to reduce the center thickness for "positive" (+) power lenses;
3. to notice the non-availability of some lenses of given diameter while the customer is still in the optician's office and thus direct the customer to select a smaller frame requiring an available diameter size; and
4. to establish a fair price or to charge an extra charge for lenses of larger diameter, because the optician knows the size of the right diameter to do the job.

Because of the multitude of frame shapes and frame sizes and the multitude of bifocal lenses available from the various manufacturer, it is almost impossible in practice to determine with precision the size of the smallest lens suitable to fit a given frame selected by a customer, unless use is made of demonstration lenses marked with a decentration cross that can subsequently be superimposed over the lens size chart of the selected manufacturer.

Still another object of the present invention is to provide a device for use in marking such decentration crosses, thereby making it possible for the optician to easily and quickly select the smallest size of uncut lens required for realizing the mounting.

It is further known that, in order to fit lenses ordered by a customer in a selected frame according to his or her P.D., segments height or height of progressive fitting crosses, the opticians also have to calculate with precision the decentration required in or out and up or down with respect to the mechanical axis of the frame, and thereafter to compensate the amount of pre-decentration on the pattern provided for cutting the lens, thereby making this operation very complicated and hazardous especially in some cases such as progressive lenses where tolerances are very strict.

To obtain such a fitting, it is necessary to decenter the optical center or the bifocal lateral center and its lenght or the fitting cross of the progressive lens according to the above mentioned calculations and to block the lens on the grinding mechanical axis.

Lens is then installed in front of the diamond wheel on an automatic edger, and pattern is installed on the same axis in front of a sensor. Different "centering and blocking devices" have been designed, such as those distributed by the French company Essilor under the trade marks "Posimatic", "Posiscope" and "Posicentron", the French company Briot-Asselin under the tradename "Centreur C 2005" and the U.S. companies Coburn-W co and A.I.T. Each of these centering and blocking devices basically comprises:

(a) a lightened screen or objective to allow optical superimposition of:
 the uncut lens; and
 the pattern on which the lens will be ground to shape;

(b) a transparent chart graduated in millimeters, having a central cross which must vertically and horizontally intersect the mechanical axis of the grinding tool;

(c) a cursor usually consisting of a yellow cross that is adjustable vertically and horizontally to indicate the calculated decentrations on the chart; and (d) a precise blocking mechanism.

These centering and blocking devices are rather efficient but none of them can be used to measure the decentration prior to blocking.

Still another object of the present invention is to provide a device that can be used for easily and precisely marking a decentration cross onto a demonstration lens that can subsequently be installed in any of the above mentioned centering and blocking devices where usually the uncut lens is installed. By superimposing the contour of the so marked demonstration lens over the contour of the pattern, it becomes possible to precisely match the cursor cross of the centering and blocking machine over the decentration cross of the lens. With such matching, calculation of the decentration is completely eliminated mistakes are avoided and precision is increased.

SUMMARY OF THE INVENTION

In accordance with the present invention, each of the above mentioned objects is achieved with an universal frame centering, holding and measuring device for use by an optician to transcribe and check a distance interpupillary distance (distance P.D.), a reading interpupillary distance (reading P.D.), a segment height, and other related measurements made onto a customer directly and precisely on a set of lenses mounted on a frame. The device comprises a base having a longitudinal axis, on which the frame may be positioned in flat position. A central pin vertically projects from the base and supports at least one vertical cylinder having such a diameter as to fit within the bridge of the frame positioned onto the base.

A frame holder is slidably mounted onto the base. This frame holder is movable along the longitudinal axis of the base and comprises a vertical front wall extending perpendicularly to the longitudinal axis of the base.

Means are provided for pressing the frame holder toward the central pin in such a manner as to hold the frame in substantially rigid position between the vertical front wall of the frame holder and the vertical cylinder mounted onto the central pin, with said vertical cylinder inserted into the bridge portion of the frame.

A pair of rulers are slidably mounted on the base. These rulers extend parallel to the longitudinal axis of the base and are symmetrically positioned with respect to the central pin in such a manner as to extend under the two lenses mounted on the frame held by the frame holder, respectively. A set of vertical graduations is provided on each ruler, each vertical graduation indicating the distance separating it from the central pin and being useful for transcribing onto the lenses, and checking, the distance P.D. or reading P.D. of the customer. A set of horizontal graduations is also provided on each ruler. These horizontal graduations are useful for transcribing on the lenses, and checking, a segment height of the customer.

In use, the device will rigidly hold the frame in centered position and will allow repositioning of the frame in the same centered position after installation of the frame on the customer's face to check the job and notice whether there is some differences in the measurement originally made onto the customer and the measurement reported onto the lenses.

Therefore, the device according to the invention can be used for holding the frame until vertical and horizontal measurements are transcribed symmetrically or subsequently adjusted on the lenses, or until monocular readings are read vertically or horizontally on the prescription lenses center of the frame installed on the device.

To mark the distance or reading vertical P.D. lines, use can be made of the set of vertical graduations provided on each ruler. To subsequently mark the horizontal lines that indicates the ideal segment height, the rulers may be slid down until the 0- horizontal graduation line of the set of horizontal graduations crosses the vertical P.D. line at its intersection with the bottom of the frame inside the ring.

BRIEF DESCRIPTION OF THE DRAWINGS

A preferred embodiment of the invention will now be described with reference to the accompanying drawings wherein.

DESCRIPTION OF A PREFERRED EMBODIMENT

Figure 1:
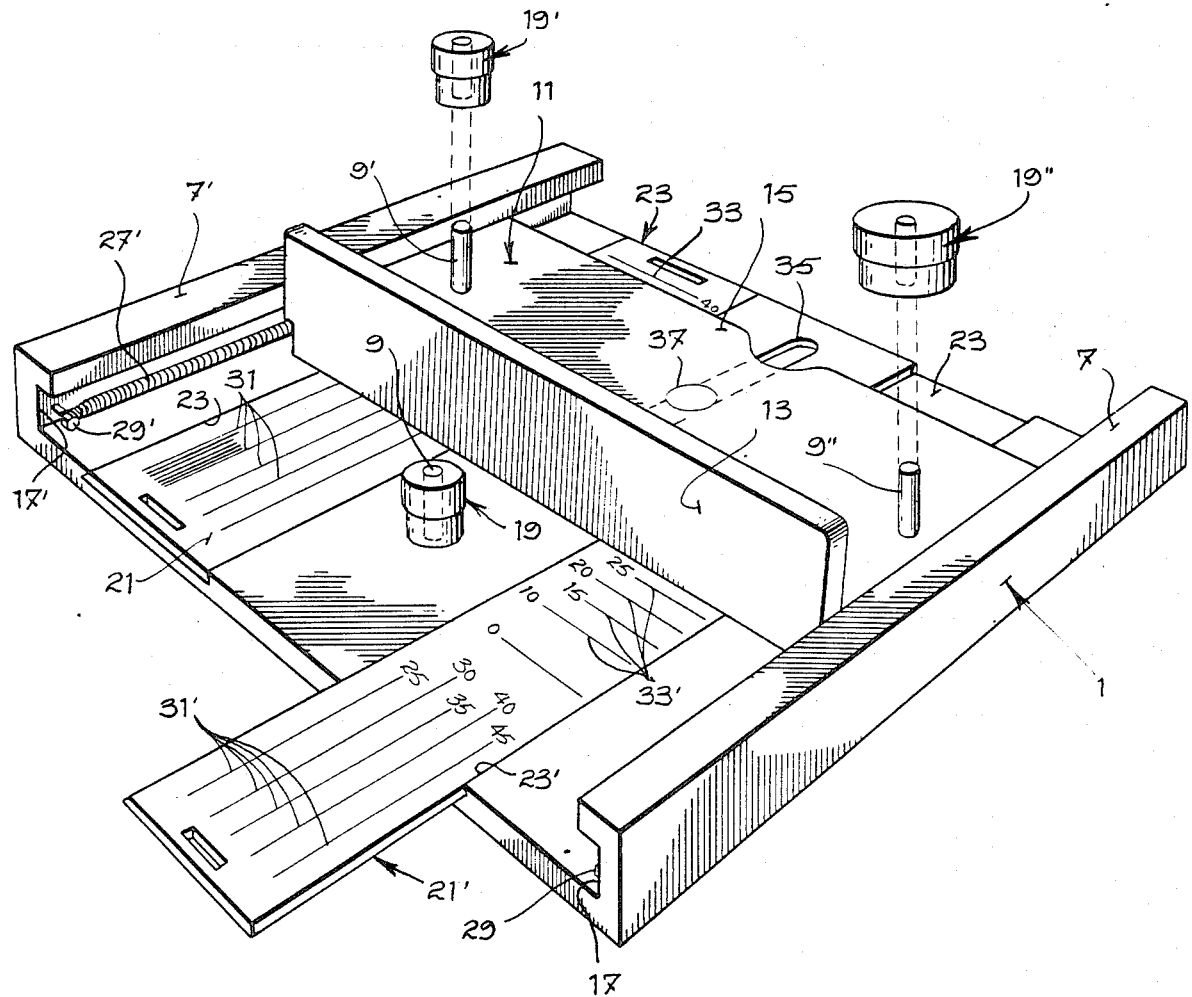
FIG. 1 is a perspective view of an universal frame centering, holding and measuring device according to the invention.
Figure 2:
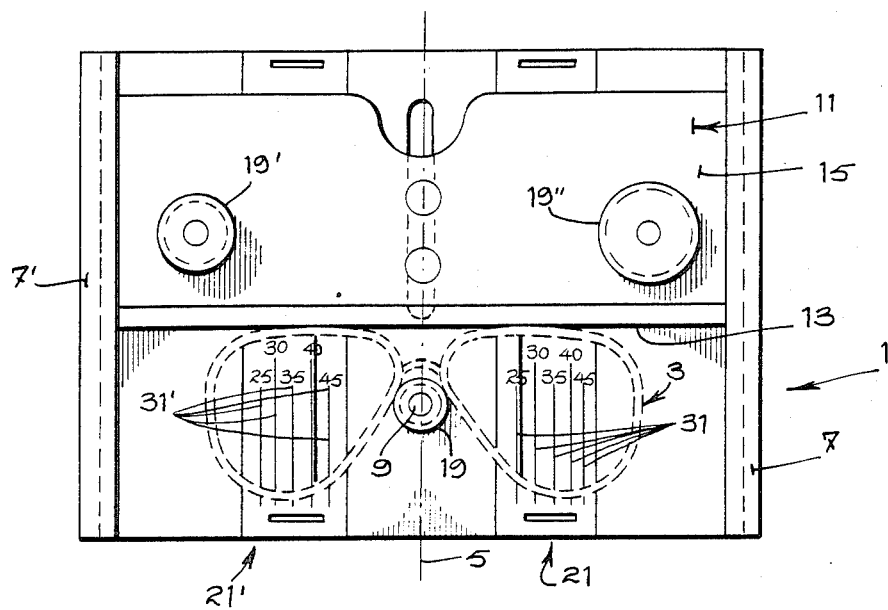
FIG. 2 is a top plan view thereof, in use for transcribing or checking onto a pair of lenses the distance P.D. or reading P.D. of a customer.
Figure 3:
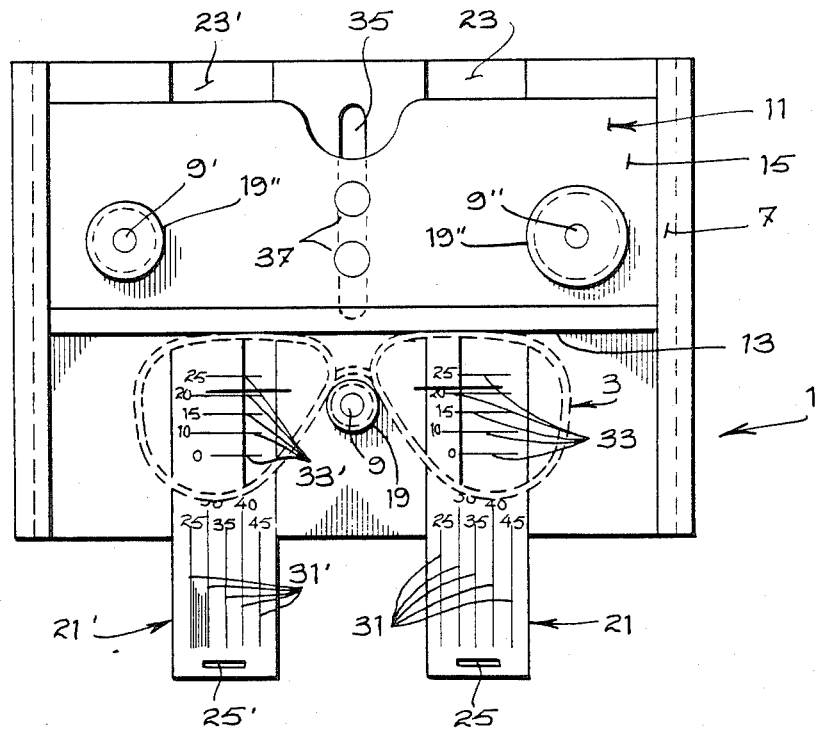
FIG. 3 is a top plan view of the device shown in FIGS. 1 and 2 in use for transcribing on the lenses and checking the segment height or the vertical reading P.D. line of a customer.

The universal frame centering, holding and measuring device as shown in FIGS. 1 to 3 of the accompanying drawings, comprises a base 1 on which a frame 3 may be positioned in flat position. The base 1 has a flat upper surface and is provided with two upwardly projecting lateral edges 7 and 7' that are parallel and symmetrically positioned with respect to a longitudinal axis 5.

The device also comprises a frame holder 11 slidably mounted onto the base 1. This frame holder 11 which is movable along the longitudinal axis 5 of the base, comprises a vertical front wall 13 extending perpendicularly to the longitudinal axis 5 and an horizontal wall 15 extending rearwardly from the vertical front wall 13 away from a central pin 9 which is positioned onto the longitudinal axis 5 and vertically projects from the upper surface of the base 1.

The frame holder 11 is slidably mounted onto the base 1 by engagement of the lateral edges of its horizontal rear wall 15, into a pair of facing grooves 17 and 17' provided in the lateral edges 7 and 7' of the base 1 (see FIG. 1). In the following description as well as in the appended claims, these grooves 17 and 17'will be referred to as the "outer" grooves of the base.

The pin 9 vertically projecting from the upper surface of the base 1 is intended to receive a vertical cylinder 19 having a central hole fitting the pin 9 and such an external diameter as to fit within the bridge of the frame 3 positioned onto the base, as clearly shown in FIGS. 2 and 3. As the shape and size of such a bridge may substantially vary from one frame to another, a set of vertical cylinders 19, 19' and 19" of different diameters may be provided, each cylinder being interchangeable onto the central pin 9 so as to fit different sizes of frame bridges. The cylinders 19' and 19" that are not in use onto the pin 9 may be positioned and stored onto a set of storing pins 9' and 9" vertically projecting from the horizontal rear wall 15 of the frame holder 11.

In order to further increase the universality and versatility of the device according to the invention, use can be made of cylinders 19, 19' and 19" each having a given external diameter at one end and another external diameter at the other end, as clearly shown in the drawings. This particular arrangement of three cylinders each with two different diameters, such as 12 and 14 mm, 16 and 18 mm and 20 and 22 mm, respectively, is sufficient, in practice, to fit any frame of common size available in the market.

As shown in the drawings, the upper surface of the base 1 may be provided with an open guiding slot 35 extending along the longitudinal axis 5 of the base and the frame holder 11 with two small pins 37 extending downwardly inside the slot 35 to guide the holder along the axis 5 and stop its movement in both directions.

Means are provided for pressing the frame holder 11 towards the central pin 9 in such a manner as to hold the frame 3 in substantially rigid position between the vertical front wall 13 of the frame holder and the vertical cylinder 19 mounted onto the central pin 9 with this vertical cylinder or one of its portion of a given diameter inserted into the corresponding bridge portion of the frame, as shown in FIGS. 2 and 3. These pressing means advantageously consist of a pair of return springs 27 and 27' positioned in the outer grooves 17 and 17' of the base 1. Each return springs 27 and 27' is preferably a tension spring having one end attached to the base 1 by means of a small pin 29 or 29', and the other end attached to the frame holder 11.

A pair of rulers 21 and 21' are slidably mounted into two dove-tail shaped, upwardly opening grooves 23 and 23' extending parallel to the longitudinal axis 5 of the base 1 in a symmetrical position with respect to the central pin 9. These grooves 23 and 23' that will hereinafter be referred to as the "inner" grooves of the base are symmetrically positioned with respect to the central pin 9 in such a manner that the rulers 21 and 21' mounted therein extend just under the two lenses mounted on the frame 3 held by the frame holder 11, respectively (see FIGS. 2 and 3).

Each ruler 21 or 21' is provided with one or more finger-nail slots 25 and 25' to make it easier to move in its corresponding groove 23 or 23'. Each ruler 21 or 21' is also provided with a set of vertical graduations 31 and 31' and with a set of horizontal graduations 33 and 33' that are preferably printed in millimeters.

The set of vertical graduations 31 and 31' which are symmetrically positioned close to one end of their respective rulers and extend from 20 to 45 mm away from the central pin 9, is intended to be used for transcribing onto the lenses and checking thereon the distance P.D. or reading P.D. measured by the optician on the customer. For this purpose, each vertical graduation of each set is identified in such a manner as to indicate the distance separating it from the central pin 9, as shown in FIG. 1. As can be understood, the distance between two graduations of the set of vertical lines of the rulers 21 and 21' is equal to the sum of the distances indicated on each graduation.

The set of horizontal graduations 33 and 33' are symmetrically positioned onto their respective rulers at a short distance over the vertical graduations for use to transcribe on the lenses and checking thereon, the segment heights measured on the customer. As shown in FIG. 3, these horizontal graduations may extend from 0 to 40 mm to accomodate all the lenses contained in any frame available in the market.

The device according to the invention as disclosed hereinabove can be used as follows:

First of all, the optician measures the interpupillary distance (distance P.D.) of his or her customer, using a small millimetric rule to do so. Then, the optician positions the customer's frame onto the device and symmetrically transcribes with the vertical graduations 31, 31' of the rulers 21, 21' the measured distance P.D. Such a transcription can be made onto the customer's frame or onto the demonstration lenses of a new frame with a fine permanent ink pen. When the vertical lines corresponding to the measured distance P.D. are marked, the optician repositions the frame onto the customer's face in order to immediately check whether the customer's interpupillary distance is symmetrical or not. If the interpupillary distance is not symmetrical, the optician may then easily notice it and correct the position of the left and right line.

If use is made of a "Pupilometer" (Essilor) to measure the distance P.D. monocularly, the measured monocular P.D. can be transcribed directly with the device onto the lenses of the customer's frame.

Similarly, using the same device with the set of horizontal graduations 33, 33' provided on each ruler 21, 21' (see FIG. 3), it is possible to transcribe the bifocal segment heights on the customer's lenses after having previously marked a pair of reading vertical P.D. lines with the vertical graduations 31 and 31' (see the crosses shown in FIG. 3). In the case of the progressive lens, marking of the height fitting cross shall however be made on the vertical distance P.D. line, as is well known by any one skilled in the art.

Once again, after transcription, repositioning of the frame with the marked lenses on the customer's face will allow the optician to notice and evaluate the amount of differences between the old and new glasses by mere alternance of the customer's face.

What is claimed is:

1. An universal frame centering, holding and measuring device for use by an optician to transcribe and check a distance interpupillary distance (distance P.D.), a reading interpupillary distance (reading P.D.), a segment height measured onto a customer, directly and precisely on a set of lenses mounted on a frame, said device comprising:

a base having a longitudinal axis, on which said frame may be positioned in flat position;

a central pin vertically projecting from the base;

at least one vertical cylinder mounted onto the central pin, said vertical cylinder having such a diameter as to fit within the bridge of the frame positioned onto the base;

a frame holder slidably mounted onto the base, said frame holder being movable along the longitudinal axis of the base and comprising a vertical front wall extending perpendicularly to the longitudinal axis of said base;

means for pressing the frame holder toward the central pin in such a manner as to hold the frame in substantially rigid position between the vertical front wall of the frame holder and the vertical cylinder mounted onto the central pin, with said vertical cylinder inserted into the bridge portion of the frame;

a pair of rulers slidably mounted on the base, said rulers extending parallel to the longitudinal axis of said base and being symmetrically positioned with respect to the central pin in such a manner as to extend under the two lenses mounted on the frame held by the frame holder, respectively;

a set of vertical graduations provided on each ruler, each vertical graduation indicating the distance separating it from the central pin and being useful for transcribing onto the lenses and checking the distance P.D. or reading P.D. of the customer; and a set of horizontal graduations provided on each ruler, said horizontal graduations being useful for transcribing on the lenses the segment heights or progressive horizontal cross line of said customer.

2. The universal device of claim 1, wherein:

the sets of vertical graduations are symmetrically positioned close to one end of their respective rulers;

the vertical graduations of each set extend from 20 to 45 mm away from the central pin;

the sets of horizontal graduations are symmetrically positioned onto their respective rulers at a short distance from the vertical graduations; and the horizontal graduations of each set extend from 0 to 40 mm.

3. The universal device of claim 2, wherein the base is provided with two outer grooves in which is slidably mounted the frame holder, and two inner grooves in which are slidably mounted the rulers, said inner grooves being upwardly opened and symmetrical with respect to the central pin.

4. The universal device of claim 3, wherein said means for pressing the frame holder toward the central pin consists of a pair return springs positioned in the outer grooves of the base.

5. The universal device of claim 4, wherein said return springs are tension springs each having one end attached to the base and the other end attached to the frame holder.

6. The universal device of claim 5, wherein the frame holder also comprises a horizontal rear wall extending from the vertical front wall away from the central pin, said horizontal rear wall having a pair of lateral edges, and wherein the frame holder is slidably mounted onto the base by mere engagement of the lateral edges of the horizontal rear wall of said holder into the outer grooves of said base.

7. The universal device of claim 4, comprising a set of vertical cylinders of different diameters, said cylinders being interchangeable onto the central pin so as to fit different sizes of frame bridge.

8. The universal device of claim 6, comprising a set of vertical cylinders of different diameters, said cylinders being interchangeable onto the central pin so as to fit different sizes of frame bridge.

9. The universal device of claim 2, wherein the vertical and horizontal graduations are millimetric.

10. The universal device of claim 8, wherein the vertical and horizontal graduations are millimetric.

11. The universal device of claim 8, comprising additional pins vertically projecting from the horizontal rear wall of the frame holder for receiving and storing the vertical cylinders that are not in use onto the central pin.

12. The universal device of claim 11, wherein each ruler is provided with a finger nail slot to make said ruler easier to move.

13. The universal device of claim 8, wherein each vertical cylinder has one given external diameter at one end and another, different external diameter at the other end.

14. The universal device of claim 6, wherein the base comprises a guiding slot extending along its longitudinal axis and the frame holder cooomprises two small pins extending downwardly inside said guiding slot, to guide said holder along the base and stop its movement in both directions.

* * * * *